United States Patent
Fiering et al.

(10) Patent No.: US 9,731,062 B2
(45) Date of Patent: Aug. 15, 2017

(54) SYSTEM AND METHOD FOR BLOOD SEPARATION BY MICROFLUIDIC ACOUSTIC FOCUSING

(75) Inventors: Jason O. Fiering, Boston, MA (US); Shivshankar Sundaram, Tampa, FL (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 592 days.

(21) Appl. No.: 13/598,401

(22) Filed: Aug. 29, 2012

(65) Prior Publication Data
US 2013/0048565 A1    Feb. 28, 2013

Related U.S. Application Data

(60) Provisional application No. 61/528,559, filed on Aug. 29, 2011.

(51) Int. Cl.
*A61M 1/36* (2006.01)
*B01J 39/00* (2006.01)
(Continued)

(52) U.S. Cl.
CPC .......... *A61M 1/3693* (2013.01); *A61M 1/362* (2014.02); *B01D 21/283* (2013.01); *G01N 33/491* (2013.01); *B01D 2221/10* (2013.01)

(58) Field of Classification Search
USPC .... 604/4.01, 891.1; 210/635, 645, 660, 690; 422/68.1, 128
See application file for complete search history.

(56) References Cited

U.S. PATENT DOCUMENTS 7,727,723 B2 * 6/2010 Pollack ............... C12Q 1/6869
422/82.05
7,815,871 B2 * 10/2010 Pamula ................... B41J 2/125
204/643
(Continued)

FOREIGN PATENT DOCUMENTS

EP    0 914 184 A1    5/1999
EP    1 809 399 B1    8/2009
(Continued)

OTHER PUBLICATIONS

International Search Report and Written Opinion issued Dec. 11, 2012 in PCT Application No. PCT/US2012/052886.
(Continued)

*Primary Examiner* — Tatyana Zalukaeva
*Assistant Examiner* — Guy K Townsend
(74) *Attorney, Agent, or Firm* — Paul Hunter; Foley & Lardner LLP

(57) ABSTRACT

Systems and methods for cleansing blood are disclosed herein. The methods include acoustically separating undesirable particles bound to capture particles from formed elements of whole blood. After introducing the capture particles to whole blood containing undesirable particles, the whole blood and capture particles are flowed through a microfluidic separation channel. At least one bulk acoustic transducer is attached to the microfluidic separation channel. A standing acoustic wave, imparted on the channel and its contents by the bulk acoustic transducer, drives the formed elements and undesirable particles bound to capture particles to specific aggregation axes. After aggregating the particles, the formed elements exit the separation channel through a first outlet and are returned to the patient. The undesirable particles, bound to the capture particles, exit through a second outlet and can be discarded to saved for later study.

49 Claims, 8 Drawing Sheets

(51) Int. Cl.
  *B01D 29/00* (2006.01)
  *B01D 12/00* (2006.01)
  *B01D 15/00* (2006.01)
  *B01D 21/28* (2006.01)
  *G01N 33/49* (2006.01)

(56) References Cited

U.S. PATENT DOCUMENTS

| | | | |
|---|---|---|---|
| 7,816,121 B2* | 10/2010 | Pollack | B01L 3/502784 204/547 |
| 7,901,947 B2* | 3/2011 | Pollack | G01N 35/10 204/450 |
| 8,083,068 B2 | 12/2011 | Kaduchak et al. | |
| 2002/0058273 A1* | 5/2002 | Shipwash | B01L 3/5027 435/6.12 |
| 2003/0175947 A1* | 9/2003 | Liu | B01F 11/0071 435/288.5 |
| 2004/0005582 A1* | 1/2004 | Shipwash | G01N 33/54366 435/6.19 |
| 2005/0106064 A1* | 5/2005 | Laurell | B01J 19/0093 422/400 |
| 2008/0154535 A1* | 6/2008 | Sparks | G05B 19/0425 702/130 |
| 2008/0181828 A1 | 7/2008 | Kluck | |
| 2008/0217259 A1* | 9/2008 | Siversson | A61M 1/3693 436/177 |
| 2010/0006501 A1 | 1/2010 | Laurell et al. | |
| 2010/0078384 A1 | 4/2010 | Yang | |
| 2010/0186524 A1* | 7/2010 | Ariessohn | G01N 1/2202 73/863.22 |
| 2010/0210989 A1* | 8/2010 | Macpherson | A61M 1/3496 604/6.03 |
| 2010/0317093 A1* | 12/2010 | Turewicz | B01L 3/50273 435/287.2 |
| 2011/0003303 A1* | 1/2011 | Pagano | B01L 3/502761 435/6.19 |
| 2011/0014297 A1* | 1/2011 | Lee | A61K 9/0009 424/491 |
| 2011/0034908 A1* | 2/2011 | Hyde | A61M 5/14276 604/891.1 |
| 2011/0045095 A1* | 2/2011 | Hettiarachchi | A61K 49/225 424/497 |
| 2011/0136262 A1* | 6/2011 | Ragavan | G01N 29/022 436/518 |
| 2012/0122084 A1* | 5/2012 | Wagner | C12N 5/0612 435/6.1 |
| 2012/0225475 A1* | 9/2012 | Wagner | G01N 15/14 435/288.7 |
| 2013/0043170 A1 | 2/2013 | Rose et al. | |
| 2013/0048565 A1 | 2/2013 | Fiering et al. | |
| 2013/0085680 A1* | 4/2013 | Arlen | G01N 27/44756 702/19 |
| 2013/0156644 A1* | 6/2013 | Lee | G01N 29/022 422/69 |
| 2014/0140891 A1* | 5/2014 | Fiering | B01L 3/502753 422/68.1 |
| 2014/0209542 A1* | 7/2014 | Spain | A61M 1/3693 210/690 |
| 2014/0248621 A1* | 9/2014 | Collins | G01N 15/1031 435/6.12 |

FOREIGN PATENT DOCUMENTS

| | | |
|---|---|---|
| EP | 2 145 687 A1 | 1/2010 |
| EP | 2 352 570 A2 | 8/2011 |
| WO | WO-02/12896 | 2/2002 |
| WO | WO-02/29400 | 4/2002 |
| WO | WO-2006/032703 | 3/2006 |

OTHER PUBLICATIONS

International Search Report and Written Opinion in PCT/US2014/022701 dated Jul. 18, 2014.
US Notice of Allowance in U.S. Appl. No. 14/168,822 dated Mar. 7, 2016.
US Notice of Allowance on U.S. Appl. No. 14/168,822 Dated Aug. 3, 2016.

* cited by examiner

A)

B)

501, 502, 503, 503

A)

B)

SYSTEM AND METHOD FOR BLOOD SEPARATION BY MICROFLUIDIC ACOUSTIC FOCUSING

CROSS-REFERENCE TO RELATED PATENT APPLICATIONS

This application claims priority from Provisional Application U.S. Application 61/528,559, filed Aug. 29, 2011, incorporated herein by reference in its entirety.

BACKGROUND OF THE DISCLOSURE

Sepsis is a disease with a very significant public health impact that has stubbornly resisted new therapies. Antibiotics are the only real therapeutic option, yet sepsis can be caused by over 100 bacteria and many fungi so a universal antibiotic is not a realistic option; the antibiotics and antifungals used have significant complications and are often unsuitable for fragile patients. The concept of cleansing the blood has been tried previously without success. Previous blood cleansing concepts have included laboratory scale methods of centrifugation, capillary electrophoresis, liquid chromatography, field flow fractionation, and liquid-liquid extraction. These devices have failed to deliver continuous flow cleansing devices. In additional to often discarding large portions of the blood, current cleansing devices may rely on: diluents, sheath flow, controlled solution conductivity, costly microfabricated on-chip materials, and toxic additives.

SUMMARY OF THE DISCLOSURE

According to one aspect of the disclosure, a blood cleansing device includes a microfluidic separation channel having an upstream portion and a downstream portion wherein the separation channel is shaped such that an interior portion of the upstream portion of the separation channel is substantially aligned with a wall of the downstream portion of the downstream portion of the separation channel. Additionally, the separation channel includes a first inlet configured to introduce flowing whole blood into the upstream portion of the separation channel. The whole blood includes plasma, a plurality of formed elements and a plurality of undesirable particles. The separation channel also includes a first outlet positioned downstream from the first inlet and upstream from the downstream portion of the separation channel, a second outlet positioned within the downstream portion of the separation channel along the wall of the downstream portion that is aligned with the interior portion of the upstream portion of the separation channel, a second inlet positioned within the separation channel between the first outlet and the second outlet, and a third outlet positioned in the downstream portion of the separation channel downstream of the second outlet.

In some implementations, the blood cleansing device includes at least a second separation channel and a third separation channel. The first outlet of the second separation channel is configured to carry fluid from the second separation channel to the second inlet of the separation channel, and the second inlet of the third separation channel is configured to receive fluid from the first outlet of the separation channel.

In some implementations, the blood cleansing device includes a microfluidic injector for introducing, into the separation channel, a plurality of lipid-based capture particles configured to bind to the undesirable particles. In some implementations, the microfluidic injector comprises one of a microfluidic nozzle and a porous membrane coupled to a lipid reservoir. In other implementations, the separation channel is formed in a substrate comprising one of polystyrene, glass, and polyimide, acrylic, polysulfone, and silicon.

In other implementations, the blood cleansing device includes an acoustic transducer positioned adjacent to the separation channel and configured to impose a standing wave transverse to the length of the upstream portion of separation channel. The wave is configured to focus formed elements and a plurality of the undesirable particles bound to a plurality of capture agents towards an interior region of the upstream portion of the channel. Some implementations include a second acoustic transducer positioned adjacent the downstream portion of the separation channel and configured to impose a standing wave transverse to the length of the second portion of the separation channel. The wave from the second acoustic transducer is selected such that the formed elements will be driven away from the wall of downstream portion of the separation channel at a rate that is faster than a rate at which the wave drives the undesirable particles bound to the capture agents away from the wall.

In some implementations, the blood cleansing device includes a second outlet positioned sufficiently downstream within the downstream portion of the separation channel that in operation, a greater percentage of the undesirable particles that are bound to the capture agents flows out of the second outlet than out of the third outlet and a greater percentage of the formed elements flows out of the third outlet than out of the second outlet.

In some implementations, the upstream portion of the separation channel comprises an aggregation point, and the upstream portion of the separation channel is configured such that a width of the first portion of the separation channel at the aggregation point is half the wavelength of the acoustic wave acting on the whole blood.

In other implementations, the separation channel comprises walls having a thickness at a particle aggregation point that is a multiple of one quarter of the wavelength of a acoustic wave acting on the walls of the separation channel. In some implementations, the height of the separation channel at a particle aggregation point is less than one quarter of the wavelength of a standing acoustic wave acting on the particle aggregation point.

According to another aspect of the disclosure, a blood cleansing device includes a microfluidic separation channel having an upstream end and downstream end. The separation channel includes a first inlet configured to introduce flowing whole blood into a proximal end of the separation channel, the whole blood including plasma, a plurality of formed elements and a plurality of undesirable particles. The separation channel also includes a first outlet at the downstream end of the separation channel positioned substantially along the longitudinal axis of the separation channel, a second outlet at the downstream end positioned adjacent a first wall of the separation channel, and a third outlet at the downstream end positioned adjacent a second wall of the separation channel, opposite the first wall. The device also includes an acoustic transducer positioned adjacent to the separation channel for imposing a standing acoustic wave transverse to a particle migration region of the separation channel, and a capture particle injector configured to introduce a plurality of lipid-based capture particles into the whole blood before the blood reaches the particle migration region of the separation channel.

In some implementations, the device comprises a reservoir in fluidic communication with the capture particle injector. In some implementations, reservoir contains a plurality of the lipid-based capture particles. In other implementations, the reservoir contains a mixture of materials, which when directed by a the capture particle injector into the whole blood, form the lipid-based capture particles. In these implementations the materials in the mixture comprise an affinity molecule, a lipid, and a fluid with a density less than 1 g/cm$^3$. In some implementations, the affinity molecule is a glycoconjugate and/or lectin. In some implementations, the lipid-based capture particles have significantly different acoustophoretic mobility than that of formed elements of blood. In some implementations, the capture particle injector comprises a microfluidic nozzle. In some implementations, the capture particle injector comprises a porous membrane. In yet other implementations, the second and third outlets merge at a fourth outlet.

According to one aspect of the disclosure, a method of cleanings blood comprises flowing whole blood, containing a plurality of undesirable particles, formed elements, and plasma, through a microfluidic separation channel. Then injecting capture particles, from a reservoir, into the separation channel such that the capture particles can bind to at least a plurality of the undesirable particles. Next, upstream of a first outlet of the separation channel, with a first standing acoustic wave, the whole blood and the captures particles are directed away from the walls of the separation channel. Then the method continues with directing, downstream of the first outlet and prior to a second outlet of the separation channel, the captures particles and the formed elements alongside a wall of the separation channel, and finally driving, prior to the second outlet, with a second standing acoustic wave, formed elements of the flowing whole blood away from the walls of the separation channel as the capture particles remain sufficiently close to the wall of the separation channel to flow out of the second outlet, while the formed elements flow out of a third outlet of the separation channel.

In some implementations, the capture particles comprise affinity molecules anchored to a lipid bilayer encapsulating a fluid. In some implementations, the fluid has a density less than about 1 g/cm$^3$.

In some implementations, the affinity molecule, lipid, and fluid are mixed in the reservoir prior to their injection into the separation channel. In some of these implementations, injecting the capture particles comprises injecting the mixture of the affinity molecule, lipid, and fluid through a nozzle such that the lipid forms a liposome surrounding the fluid. In some implementations, the capture particle comprises a polystyrene bead. In yet other implementations, the capture particles have significantly different acoustophoretic mobility than that of formed elements of blood. In some implementations, the capture particles are less about 10 μm and greater than about 2 μm in diameter.

In some implementations, the formed elements of blood comprises at least one of red blood cells, white blood cells, and platelets. In some implementations, the method further comprises unbinding the capture particles from the undesirable particles after flowing through the third outlet and introducing the unbound capture particles into the separation channel.

In other implementations, the formed elements are driven away from the walls at a faster rate than the capture particles and undesirable particles by the standing acoustic wave. In some implementations, the method further comprises extracting whole blood from a patient prior to flowing the whole blood through the separation channel, the extracted whole blood having a first concentration of undesirable particles, and then reintroducing whole blood with fewer undesirable particles back into the patient after flowing whole blood through the plurality of microchannels.

According to another aspect of the disclosure, a method of cleansing blood comprises flowing a suspension through a microfluidic separation channel, the suspension including a plurality of target particles having a positive acoustic contrast factor and a plurality of undesirable particles suspended in a fluid. Introducing into the suspension a plurality of positive contrast-factor capture particles selected to bind to the undesirable particles, wherein the magnitude of the positive contrast-factor of the capture particles is substantially different than that of the target molecules. Applying a standing acoustic wave across the separation channel transverse to the direction of the flow of the suspension through the separation channel such that a pressure node forms along an interior axis of the separation channel, and collecting the positive-factor capture particles through an outlet of the separation channel at a distance along the separation channel that is sufficiently beyond the point in the channel at which the standing acoustic wave is introduced that the target particles are separated from the positive-factor capture particles.

According to another aspect of the disclosure, a method of cleansing blood comprises flowing whole blood, including plasma, a plurality of formed elements, and a plurality of undesirable particles, into an inlet of a microfluidic separation channel, introducing a plurality of lipid-based capture particles into the whole blood such that the lipid-based capture particles bind to a plurality of the undesirable particles, applying a standing acoustic wave transverse to a direction of flow of the whole blood through the separation channel such that the formed elements aggregate to about the axial center of the separation channel and the capture particles aggregate along at least one wall of the separation channel, collecting formed elements of the whole blood at a first outlet positioned at a downstream end of the separation channel at about the axial center of the separation channel, and then collecting capture particles through at least a second outlet positioned at the downstream end of the separation channel adjacent to the at least one wall along which the capture particles are aggregated.

In some implementations, at least one wall comprise at least one side wall of the separation channel, at least one of the top walls, and/or bottom walls of the separation channel. In some implementations, the capture particles comprise affinity molecules anchored to a lipid bilayer encapsulating a fluid. In some implementations, the fluid has a density less than 1 g/cm$^3$. In other implementations, the affinity molecule, lipid, and fluid are mixed in the reservoir prior to their injection into the separation channel. In some implementations, injecting the capture particles comprises injecting the mixture of the affinity molecule, lipid, and fluid through a nozzle such that the lipid forms a liposome surrounding the fluid. In some implementations, the capture particle comprises a polystyrene bead. In some implementations, the capture particles have significantly different acoustophoretic mobility than that of formed elements of blood. In some implementations, the capture particles are less than 5 μm or 2 μm in diameter. In some implementations, the formed elements of blood comprises at least one of red blood cells, white blood cells, and platelets. In some implementations, the method further comprises, extracting whole blood from a patient prior to flowing the whole blood through the separation channel, the extracted whole blood having a first concentration of undesirable particles, and reintroducing whole blood with fewer undesirable particles back into the patient after flowing whole blood through the plurality of microchannels.

According to another aspect of the disclosure, a method of cleansing blood comprises flowing a suspension, including a plurality of target particles and a plurality of undesirable particles suspended in a fluid into an inlet of a microfluidic separation channel. Introducing into the suspension a plurality of lipid-based capture particles such that the lipid-based capture particles bind to a plurality of the undesirable particles, and applying a standing acoustic wave transverse to a direction of flow of the suspension through the separation channel such that the target particles aggregate to about the axial center of the separation channel and the capture particles aggregate along at least one wall of the separation channel.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION OF THE PREFERRED EMBODIMENTS

The various concepts introduced above and discussed in greater detail below may be implemented in any of numerous ways, as the described concepts are not limited to any particular manner of implementation. Examples of specific implementations and applications are provided primarily for illustrative purposes.

The present system and methods described herein generally relates to a system for cleansing blood. Accordingly, in various implementations, the disclosure relates to the cleansing of whole blood by acoustically separating undesirable particles from the blood via high throughput microfluidic arrays. In certain implementations, in part to overcome the prior deficiencies with the poor performance of acoustic separation on small particles, prior to acoustic separation of the blood, capture particles are introduced and mixed with the blood to form complexes with the undesirable particles, yielding particles large enough to be effectively and efficiently targeted by acoustic separation.

Figure 1:
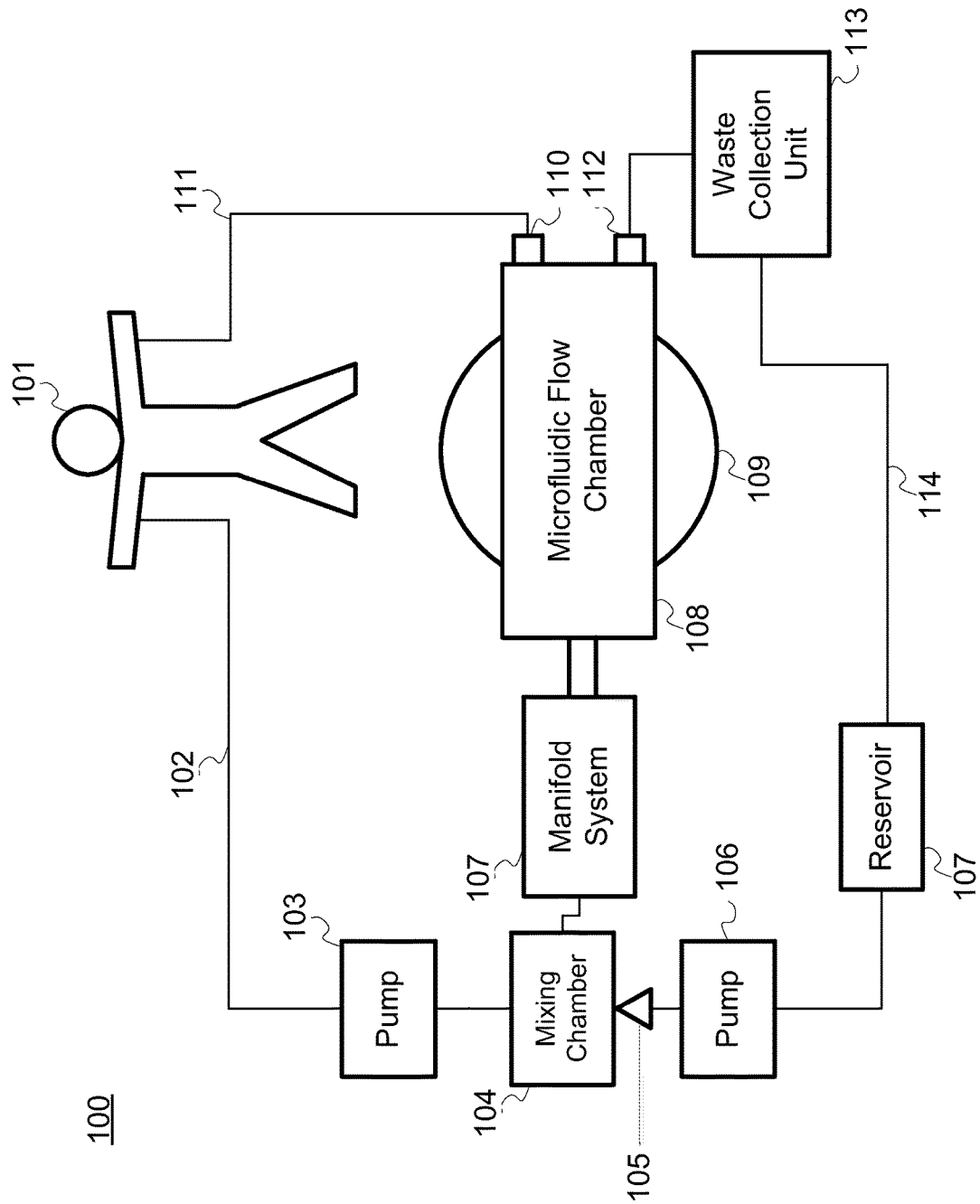
FIG. 1 is a block diagram of a system for cleansing blood, according to one illustrative embodiment.

FIG. 1 illustrates a system 100 for cleansing blood by removing waste material such as bacteria, viruses and toxins. In the system 100, blood is removed from a patient via an intravenous line 102. The blood is then pumped to a mixing chamber 104 by a first pump 103. In the mixing chamber 104, capture particles are mixed with whole blood. The components of the capture particles are stored in a reservoir 107. From the reservoir 107, the capture particles are pumped by a second pump 106 into the mixing chamber. The capture particles are formed as the contents of the reservoir 107 are extruded from a micronozzle 105 at the entrance to the mixing chamber 104. From the mixing chamber 104, the whole blood and capture particles enter a manifold system 107. The manifold system 107 distributes the whole blood and capture particles to a plurality of separation channels contained within the microfluidic flow chamber 108. The microfluidic flow chamber 108 sits atop at least one bulk piezoelectric acoustic transducer 109. The acoustic waves generated by the bulk piezoelectric acoustic transducers are used to funnel the contents of the whole blood and capture particles to specific outlets of the separation channels. As the whole blood flows through the microfluidic flow chamber 108, cleansed blood flows to a first outlet 110. After exiting the first outlet 100, the cleansed blood returns to the patient 101, via a second intravenous line 111. The capture particles and other waste material removed from the blood exit the microfluidic flow chamber 108 via a second outlet 112. Next, the waste material and capture particles enter a waste collection unit 113. In the waste collection unit 113, the capture particles are separated from the waste material. Once separated, the waste material is discarded and the capture particles are returned to the reservoir 107 by tubing 114. Once returned to the reservoir 107, the capture particles are reused in the system to remove additional waste material from whole blood as it continues to flow through the system.

The system 100, as illustrated, includes a pump 103 for moving blood from the patient 101 to the mixing chamber 104. In some implementations, the pump operates continuously, while in other implementations the pump works intermittently, and only activates when the level of whole blood in the mixing chamber 104 or manifold falls below a set threshold. In some implementations, the flow rate of the pump is configurable, such that the rate the blood exits the patient can be configured to be faster or slower than if no pump was used. In yet other implementations, no external pump is required. In this example, the blood is transported to the mixing chamber 104 by the pressure generated by the patient's own heart. In some implementations, the patient 101 is connected to a blood pressure monitor, which in turn controls the pump. Example pumps can include, but are not limited, to peristaltic pumps or any other pump suitable for flowing blood.

As illustrated in the system 100, capture particles are also pumped into the mixing chamber. A second pump 106 pumps the ingredients to form the capture particles from a reservoir 107 to the mixing chamber 104. In some implementations, the components of the capture particles are continuously agitated in the reservoir 107 in order to keep the components well mixed. The components are formed into capture particles as they enter the mixing chamber 104. The components enter the mixing chamber 104 through a micronozzle 105. In some implementations, the micronozzle 105 injects the capture particles into the mixing chamber 104. In other implementations, the micronozzle 105 injects the capture particles into the manifold system 107, and in yet other implementations the micronozzle 105 is positioned such that it injects capture particles directly into the separation channels of the microfluidic chamber 108. In some implementations, the micronozzle 105 is a micro-machined nozzle, configured to allow a specific amount of the capture particle components through the nozzle at a given time. In some implementations, the micronozzle is an array of micronozzles. In yet other implementations, the micronozzle is a membrane with pores. The pump 106 is configured to flow the contents of the reservoir through the micronozzle 105 at a predetermined rate such that the amphipathic characteristics of the molecules of the components of the captures particles cause the capture particles to spontaneously form as they exit the micronozzle 105.

In some implementations, a micronozzle is not used to generate the capture particles. In these implementations, the capture particles are premade. The capture particles are then stored in the reservoir and then introduced into the system by the pump 106 at either the mixing chamber 104, manifold system 107, and/or the separation channels of the microfluidic flow chamber 108.

As illustrated in system 100, the whole blood containing undesirable particles and the capture particles enter the mixing chamber 104. In some implantations, the contents of the mixing chamber are continuously agitated to improve distribution of the capture particles throughout the whole blood and undesirable particles such that the capture particles bind to the undesirable particles. In some implementations, anticoagulants or blood thinners are introduced into the mixing chamber 104 to assist the blood as it flows through the system 100. In some implementations, the mixing chamber 104 contains a heating element for warming the contents of the mixing chamber 104.

The contents of the mixing chamber 104 then flow into the manifold system 107, as illustrated by system 100. The manifold system 107 flows the whole blood, undesirable particles, and capture particles into the inlets of the plurality of separation channels of the microfluidic flow chamber 108.

In the illustrated system 100, the microfluidic flow chamber 108 contains a plurality of separation channels. The capture particles and undesirable particles are driven with standing acoustic waves to outlets. In some implementations, the separation occurs during a single stage, while in other implementations, the separation occurs over a plurality of stages. In some implementations, the microfluidic flow chamber is disposable.

As show in the illustrations of system 100, the microfluidic flow chamber 108 sits atop a bulk piezoelectric acoustic transducer 109. In some implementations, the system 100 contains a single bulk piezoelectric acoustic transducer 109, while in other implementations the system 100 contains a plurality of bulk piezoelectric acoustic transducers 109.

In some implementations, the bulk piezoelectric acoustic transducer 109 is glued to the microfluidic flow chamber 108. In other implementations the microfluidic flow chamber 108 is clamped to the bulk piezoelectric acoustic transducer 109 so the microfluidic flow chamber may easily be removed from the system. In other implementations the adhesive material connecting the bulk piezoelectric acoustic transducer 109 to the microfluidic flow chamber 108 is removable, for example by heating the adhesive.

The bulk piezoelectric acoustic transducer 109 imposes a standing acoustic wave on the separation channels of the microfluidic flow chamber 108 transverse to the flow of the fluid within the microfluidic flow chamber 108. The standing acoustic waves are used to drive fluid constituents towards or away from the walls of the separation channels or other aggregation axes.

Figure 5:
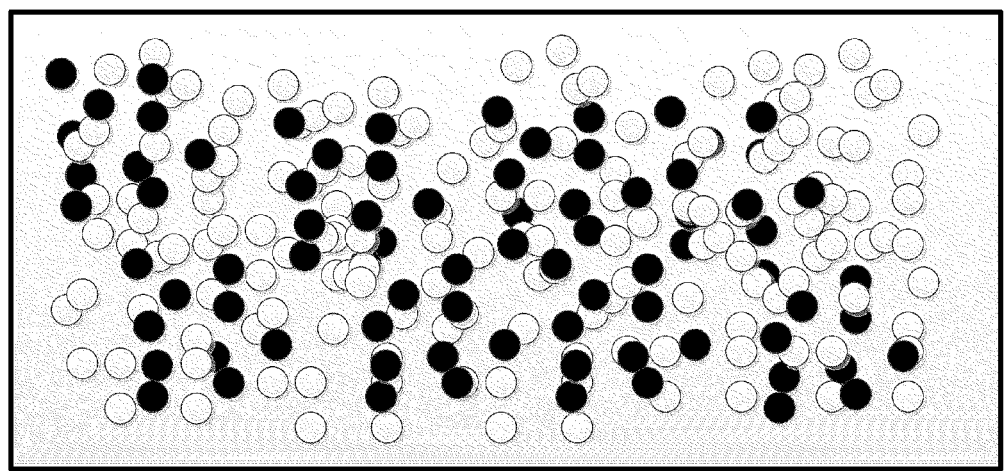
FIG. 5A is a cross sectional view a single-stage separation channel, as depicted in FIG. 2, containing a plurality of particles lacking an active acoustic transducer, according to one illustrative embodiment.
FIG. 5B is a cross sectional of a single-stage separation channel, as depicted in FIG. 2, containing a plurality of particles adjacent to an active acoustic transducer, according to one illustrative embodiment.
Figure 5:
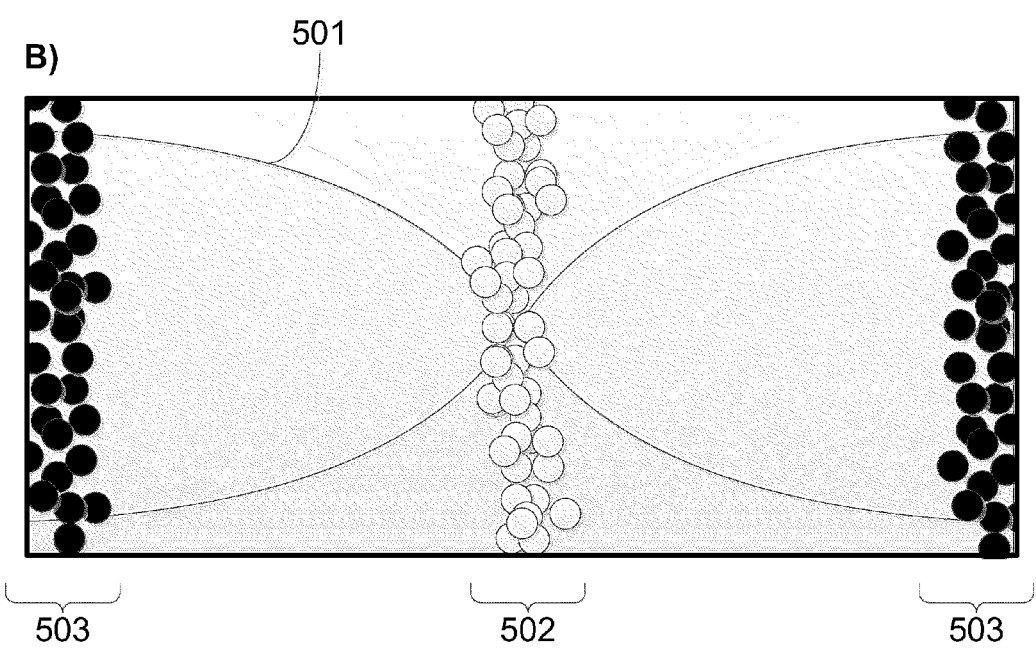

More particularly, the dimensions of the separation channels are selected based on the wavelength of the imposed standing wave such a pressure node exists at about the center or other interior axis of the separating channel, while antinodes exists at about the walls of the separation channel. Particles are driven to different positions within the channel based on the sign of their acoustic contrast factor at a rate which is proportional to the magnitude of their contrast factor. Particles with a positive contrast factor (e.g. the formed elements of blood) are driven towards the pressure node within the interior of the separation channel. In contrast, particles with a negative contrast factor are driven toward the pressure antinodes. These principles are depicted and described further in relation to FIGS. 5A and 5B.

Based on these principles, formed elements of blood can be separated from capture particles (and thus the undesirable particles bound to the capture particles) in two ways. In one way, as described further in relation to FIGS. 2 and 10, capture particles are selected to have negative contrast factors, which is opposite to the positive contrast factors of the formed elements of blood. Thus, in response to the standing acoustic wave, the formed elements are driven towards the resulting pressure node while the capture particles are driven towards the antinodes.

This technique can be used in a single-stage separation system. As whole blood, undesirable particles and capture particles mix in the mixing chamber 104 and continue to mix as flowing through the manifold system 107, the capture particles bind to the undesirable particles. As the whole blood, undesirable particles and capture particles enter the area of the separation channel where the standing acoustic wave is imparted, the standing acoustic wave drives the capture particles and bound undesirable particles to a specific axis (e.g., against the wall of the separation channel) and the formed elements of the whole blood to a second axis (e.g., the middle of the separation channel). Thus, the capture particles and undesirable particles can be collected from the edges of the separation channel and disposed of while the cleaned blood is collected and returned to the patient.

Alternatively, capture particles can be separated from formed elements of blood based on a time of flight principle. That is, if the capture particles are selected to have a contrast factor that is the same sign as that of the formed elements of blood, but with a substantially different magnitude, and assuming the formed elements and capture particles are substantially aligned prior to the application of a standing wave at a distance away from the positive pressure node induced by the wave, the formed elements and capture particles will migrate towards the pressure node at different rates. Thus, the formed elements and capture particles can be collected separately at a point where the higher contrast factor particles (capture particles or formed elements depending on the selected capture particles) have move sufficiently far from the initial aggregation axis that they have separated from the capture particles due to their difference in acoustophoretic mobility. Thus, in some implementations, a two-stage separation process is employed. In the two-stage process, formed elements of blood and capture particles are first aggregated along a common first axis of the separation channel using a first standing acoustic wave. Then after they have reached the common aggregation axis, a second standing acoustic wave drives the formed elements and capture particles to a second aggregation axis. However, instead of waiting until the formed elements and capture particles all reach the second aggregation axis, the channel splits to direct the particles having the lower acoustophoretic mobility down a first outlet. The particles that have a greater acoustophoretic mobility, which would have already migrated towards the second aggregation axis to a point that they are beyond entrance to the first outlet, flow out a second outlet. This separation technique is described further in relation to FIGS. 3 and 10.

As illustrated in the system 100, the cleansed blood exits the microfluidic flow chamber 108 at a first outlet 110. From there the blood is returned to the patient 101 via an intravenous supply line 111. In some implementations, the blood in the supply line 111 is reheated to body temperature before returning to the patient 101. In other implementations an infusion pump is used to return the blood to the patient 101, while in the system 100 the pressure generated in the system by pumps 103 and 106 is adequate to force the blood to return to the patient 101.

As illustrated in the system 100, waste material (e.g. the capture particle and undesirable particles) exit the microfluidic flow chamber 108 and enter a waste collection unit 113. In some implementations, the waste collection unit 113 contains a capture particle recycler. The capture particle recycler unbinds the undesirable particles from the capture particles. The capture particles are then returned to the reservoir 107 via tubing 114. The undesirable particles are then disposed of. In some implementations, the undesirable particles are saved for further testing.

While the system 100 is described above for the in-line cleansing of a patient's blood, in alternative implementations, the system 100 can be used to cleanse stored blood. For example, the system 100 can be used to cleanse collected blood for later infusion to help ensure the safety of the blood.

Figure 2:
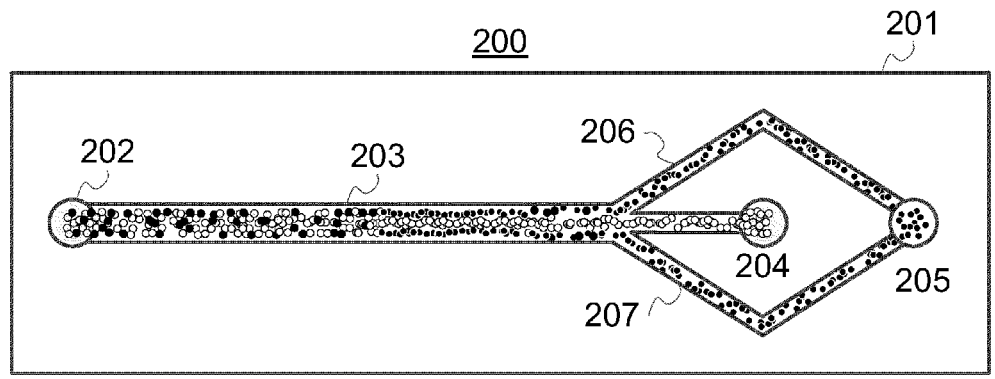
FIG. 2 is a top view of a single-stage separation channel, such as can be used in the system of FIG. 1, according to one illustrative embodiment.

FIG. 2 illustrates an example single-stage separation channel suitable for use within the microfluidic flow chamber 108 of the blood cleansing system 100. The separation channel includes an inlet 202, a flow channel 203, a first outlet 204, a first outlet channel 206, a second outlet channel 207, and a second outlet 205. The separation channel is manufactured in a sheet of material 201.

In FIG. 2, whole blood, undesirable particles, and capture particles enter the separation channel at the inlet 202 from the manifold system 107. The whole blood, undesirable particles, and capture particles then flow the length of the flow channel 203. The flow channel is subdivided into three regions: an upstream region, a downstream region, and a migration region. The migration region lies between he upstream and downstream regions, and is the region of the flow channel where the standing acoustic wave is imparted transverse to the flow of particles. As the formed elements of the whole blood, capture particles and the undesirable particles enter the migration region, the standing acoustic wave drives the capture particles bound to the undesirable particles to the side walls of the separation channel, and the formed elements of the whole blood to the center of the channel. The formed elements of the whole blood then exit the separation channel through the outlet 204 located at about the central axis of the separation channel. The capture particles and undesirable particles then exit the separation channel through the first and second outlet channels 206 and 207 which terminates in the second outlet 205. In some implementations, the formed elements are driven to the walls of the separation channel and the capture and undesirable particles remain in the center of the separation channel.

In some implementations, the separation channel 200 can separate undesirable particles from any fluid. As discussed above and later in relation to FIGS. 5 and 7, the separation channel 200 can be used to remove undesirable particles from any fluid, so long as the characteristics of the capture particle are appropriately selected. For example, selecting an encapsulated fluid such that its density and bulk modulus gives the capture particle a contrast factor that distinguishes it from the fluid and other particles in the fluid. For example, the separation channel 200 may be used to remove undesirable particles from, but not limited to, blood plasma, blood serum, water, liquid food products (e.g., milk), and lymph.

In the implementation of FIG. 2, the outlet 205 is formed from the merging of two outlet channels 206 and 207. In some implementations, the streams do not rejoin, but lead to separate outlet terminals.

In FIG. 2, the particles are separated in the same plane as the sheet of material 201 (i.e. particles are aligned to the left, right, or center of the channel); however, in other implementations, the particles are separated out of plane. For example, in some implementations, the particles are aligned with the top, middle, or bottom of the channel.

In FIG. 2, the sheet of material 201 can include, but is not limited to, polystyrene, glass, polyimide, acrylic, polysulfone, and silicon. The channel can be manufactured by a number of manufacturing techniques, including, but not limited to, milling, embossing, and etching.

Figure 3:
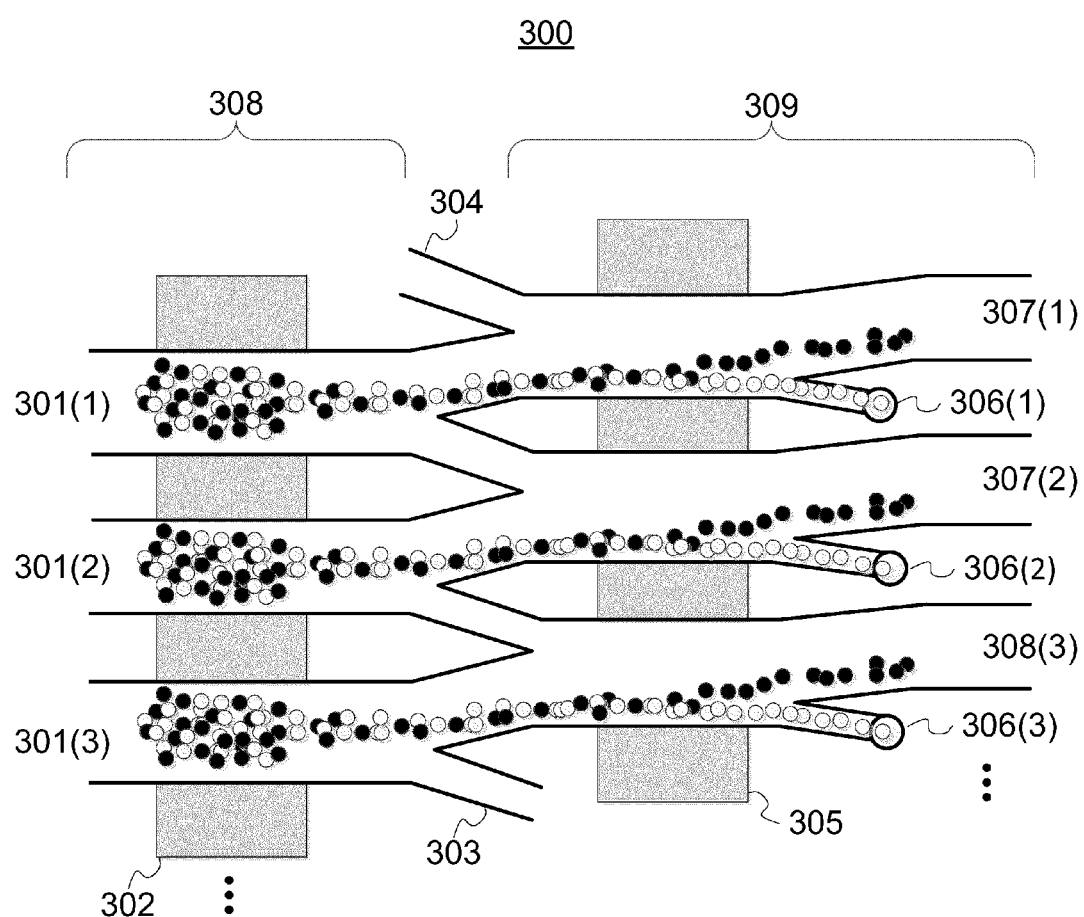
FIG. 3 is a top view of a network of two-stage separation channels, such as can be used in FIG. 1, according to one illustrative embodiment.

FIG. 3 illustrates an example network 300 of multistage separation channels suitable for use the blood cleansing system 100 depicted in FIG. 1. The network of separation channels includes a plurality of first inlets 301. FIG. 3 also includes first and second acoustic bulk transducers 302 and 305, respectively. Additionally, each separation channel includes an upstream outlet 303 and a second inlet 304. The upstream outlet 303 of each channel is connected to the second inlet 304 of its neighboring channel. The fluid exits the separation channels through a first downstream outlet 307 or second downstream outlet 306.

In each separation channel of the network 300, the flow channel through which most of the fluid in the channel flows shifts after the upstream outlet 303. The portion of the separation channel prior to the shift is referred to as the upstream portion 308 and the portion after the shift is referred to as the downstream portion 309. As the particles within the blood continue to flow down the separation channel, one subset of particles is driven into a first downstream outlet 307 and a second subset of the particles are driven into a second downstream outlet 306. For example, the cleaned blood exits through the first downstream outlet 307 and the capture particles with bound undesirable particles exits through the second downstream outlet 306.

As described above, and illustrated in FIG. 3, the separation channels in the network 300 are generally divided into upstream portions 308 and downstream portions 309. The two portions are distinguished by a shift in the separation channel. The angle of the shift is referred to as the branching angle. The branching angle for a particular implementation is chosen to substantially align a wall of the downstream portion 309 with an interior axis of the upstream portion 308. The selected axis corresponds to the location of a pressure node induced in the channel by the first acoustic transducer 302. For example, in some implementations, a wall of the downstream portion 309 is configured to align with an interior axis substantially in the middle of the upstream portion 308.

In the illustration of FIG. 3, there are a plurality of first inlets 301. The number of first inlets, and thus separation channels, can be increased to n where n is the number of separation channels required to meet the flow demands of a specific implementation. In some implementations, the first inlets 301 are configured to accept flowing whole blood and a plurality of capture particles. The flowing whole blood includes plasma, a plurality of formed elements and a plurality of undesirable particles. The formed elements of blood can include leukocytes (white blood cells), erythrocytes (red blood cells), and thrombocytes (platelets). In some implementations, the capture particles begin binding to the undesirable particles as they are mixed as they flow down the length of the upstream portion 308. In other implementations, the capture particles are mixed with the whole blood prior to flowing through the first inlet 301, and thus the binding of the capture particles and undesirable particles can begin before the blood is flowed through the first inlet 301.

As the fluid in the separation channels flows downstream it passes over a first bulk acoustic transducer 302 and eventually a second bulk acoustic transducer 305. The bulk acoustic transducers 302 and 305 impart standing acoustic waves on the separation channels. The standing acoustic waves are transverse to the flow of fluid through the separation channels. In some implementations, the acoustic bulk transducers 302 and 305 emit standing acoustic waves of different wavelengths. In other implementations the acoustic bulk transducers 302 and 305 emit standing acoustic waves of the same wavelength. Example acoustic waves can have, but are not limited to, wavelengths between about 1 and about 4 MHz.

In the network 300, the first acoustic bulk 302 transducer aligns the formed elements, capture particles, and undesirable particles in the interior of the upstream portions 308 of the separation channels. After the particles in the fluid are aligned in the middle of the flow channels, the channels angle to align the particles with walls of the downstream portions 309. With all particles aligned in the middle of the flow channel, fluid substantially away from the middle is free of capture particles and undesirable particles. Thus, at the angle in the flow channels, a portion of the fluid, substantially void of formed elements, capture particles and undesirable particles, exits through the upstream outlets 303. The particles continue to flow downstream, now substantially aligned with a wall of the respective downstream portions 309. Fluid entering the downstream portions 309 of the separation channels from the second inlets 304 ensures continued flow of the formed elements and capture particles through the downstream portions of the 309 of the separation channels.

In the second stage particles are separated based on the speed at which (and thus distance) they travel from a given aggregation axis towards a second pressure node induced in the channel by a second standing acoustic wave. As indicated above, due to the angling of the separation channels, the formed elements and capture particles enter the downstream portions of the separation channels aggregated along one wall.

As the particles flow along the wall of the separation flow channels, they pass over a second bulk transducer 305, which emits a second standing acoustic wave transverse to the flow of the particles. The second standing acoustic wave drives the particles away from the wall. Based on the magnitude of their contrast factor, a first subset of particles (e.g., the formed elements of blood) moves away from the wall at a faster rate then a second subset of particles (e.g., the capture particles).

This differential rate of movement is achieved by using capture particles that have an acoustophoretic mobility that is substantially different from that of the formed elements of blood. The different acoustophoretic mobility is in turn based on the magnitude of the contrast factor of capture particles being substantially different from the magnitude of the contrast factor of the formed elements of blood. The speed at which the two groups move away from the wall can be calculated, and the rate of flow of blood through the system is known. Thus, the distance the formed elements will be moved away from the wall of a separation channel at a given location after being exposed to the second acoustic standing wave can also be calculated. This distance is termed d(f, x), where d is the distance traveled away from the wall given a specific fluid flow rate (f) and a specific distance (x) after the application of the standing acoustic wave. Based on this calculation, the separation channel can be divided into two outlets. The second downstream outlet 306 is positioned along the wall the formed elements and capture particles were previously flowing. The second downstream outlet 306 is constructed to have a width just smaller than d(f, x). Thus, the formed elements, having traveled a distance of d(f, x) away from the wall due to the second standing acoustic wave would have been driven beyond the second outlet by the time they reach the distance (x), and thus are driven into the first downstream outlet 307. In contrast, the capture particles bound to the undesirable particles, having traveled a distance substantially less than d(f, x) due to their lesser acoustophoretic mobility, remain substantially near the wall of the downstream portion 309 and exit the second outlet 306. In some implementations, the distance (x) traveled between exposure to the standing acoustic wave and entering the first downstream outlet 307 is between about 1 and about 10 cm.

Figure 4:
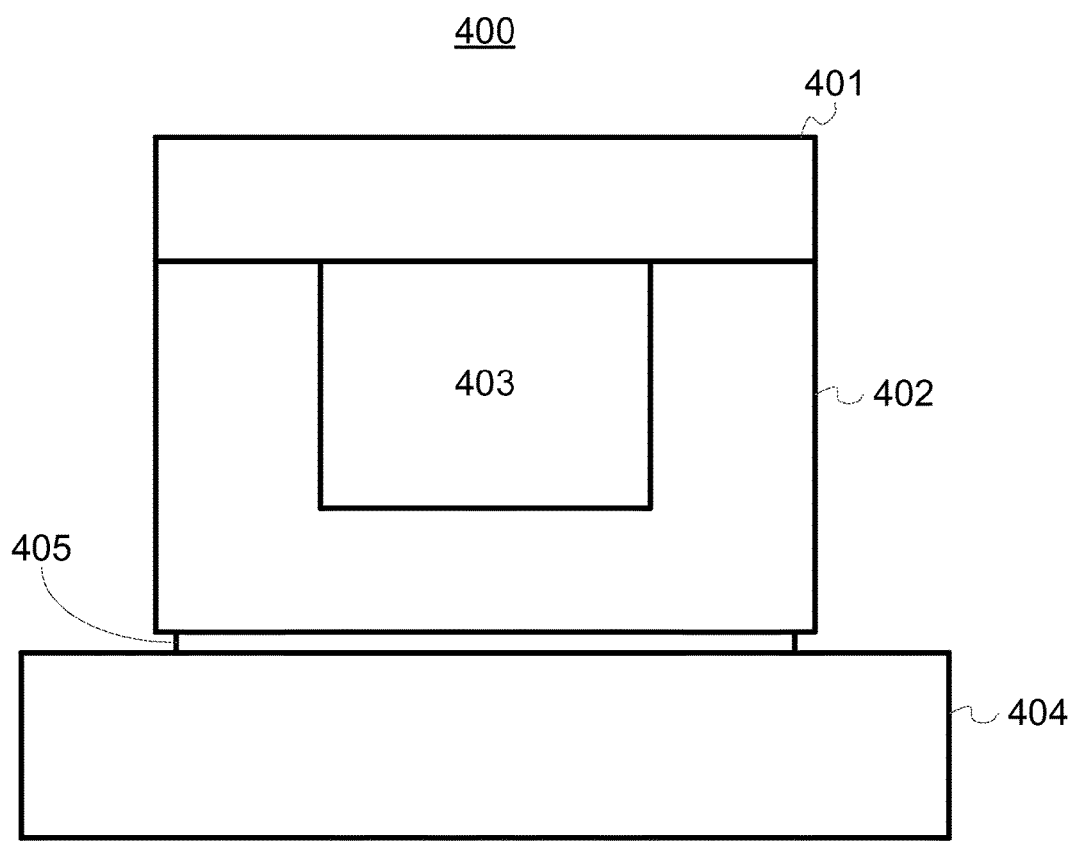
FIG. 4 is a cross sectional view of a single-stage separation channel, such as the separation channel of FIG. 2, mounted to a bulk transducer, according to one illustrative embodiment.

FIG. 4 is an illustrative cross-section of a separation channel 400 similar to the separation channel depicted in FIG. 2. The separation channel 400 includes a top layer 401 sitting atop a bottom layer 402. A channel is created in the bottom layer 402. When the top layer 401 is placed on the bottom layer 402 a lumen 403 is created. The separation channel 400 sits atop a bulk piezoelectric transducer 404.

The separation channel 400 is secured to the bulk transducer 404, by a coupling adhesive 405 and/or mechanical clamp. In some implementations, the coupling adhesive is cyanoacrylate glue.

The bottom layer 402 and top layer 401 of the separation channel 400 are manufactured from a substrate sheet. The substrate sheet can be made of, without limitation, polystyrene, glass and polyimide, polyacrylic, polysulfone, and silicon. In some implementations, the bottom layer 402 is manufactured by milling, embossing, and/or etching. After creating the two layers, they can be joined together by thermacompression, mechanical clamping, adhesive bonding, and/or plasma bonding. As described above, the separation channel sits atop a acoustic bulk transducer 404. The transducer 404 imparts a standing acoustic wave of a specific wavelength ($\lambda$) across the channel. The dimensions of the bottom layer 402, top layer 401, and lumen 403 are dependent on the selected wavelength. The width of the lumen 403 is equal to about half the wavelength ($\lambda_{fluid}/2$) of the acoustic wave in the fluid. The thickness of the side wall is equal to about a multiple of one quarter of the wavelength ($n \times \lambda_{wall}/4$) of the acoustic wave in the solid channel wall. The height of the lumen is preferably less than one quarter of the wavelength ($<\lambda_{fluid}/4$) of the acoustic wave in the fluid, and the thickness of the top layer 401 can be arbitrarily selected; however, in some implementations is chosen to be greater than one quarter of the wavelength ($>\lambda_{wall}/4$) of the acoustic wave in the solid channel wall.

FIGS. 5A and 5B are cross sectional views of particles suspended in a fluid as they flow through a separation channel similar to the separation channel 200. For FIGS. 5A and 5B, the flow of the fluid is transverse to the plane of the drawings. In some implementations, the fluid is whole blood, and the particles are the formed elements and capture particles. For illustrative purposes, FIGS. 5A and 5B contains two particles, red blood cells (white dots) and capture particles (black dots). FIG. 5A illustrates blood flowing through a channel without a standing acoustic wave being imparted on the channel and its contents. In FIG. 5A, the particles remain homogenously mixed throughout the channel. In FIG. 5B, a standing wave is imparted on the channel. The standing acoustic wave 501 creates two node types. A pressure node occurs at 502. The node extends across the full height of the lumen. The channel dimensions set forth above in relation to FIG. 4 yield a pressure node at approximately the center of the channel.

Particles are aligned based on the sign of their contrast factor. Particles with a positive contrast factor (e.g. the formed elements of blood) are driven towards a pressure node 502. In contrast, particles with a negative contrast factor (e.g. capture particles used in the single-stage device described above) are driven toward the pressure antinodes 503.

Figure 6:
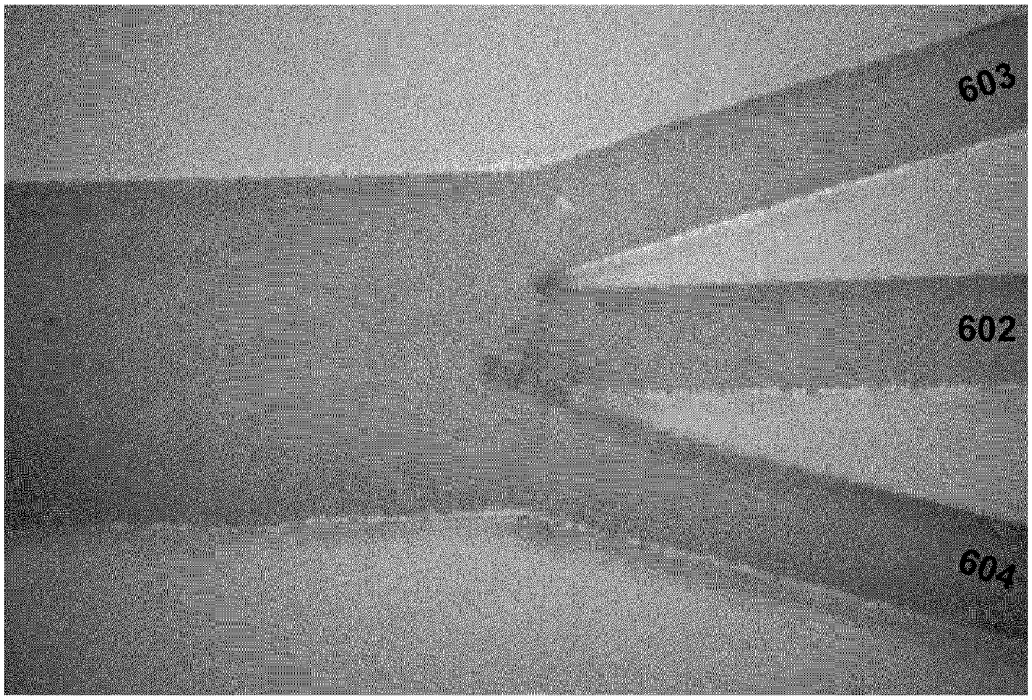
FIG. 6A is a top view of a separation channel, as depicted in FIG. 2, in which fluid is flown through the channel without the application of the standing acoustic wave.
FIG. 6B is a top view of a separation channel, as depicted in FIG. 2, after the application of a standing acoustic wave, according to one illustrative embodiment.
Figure 6:
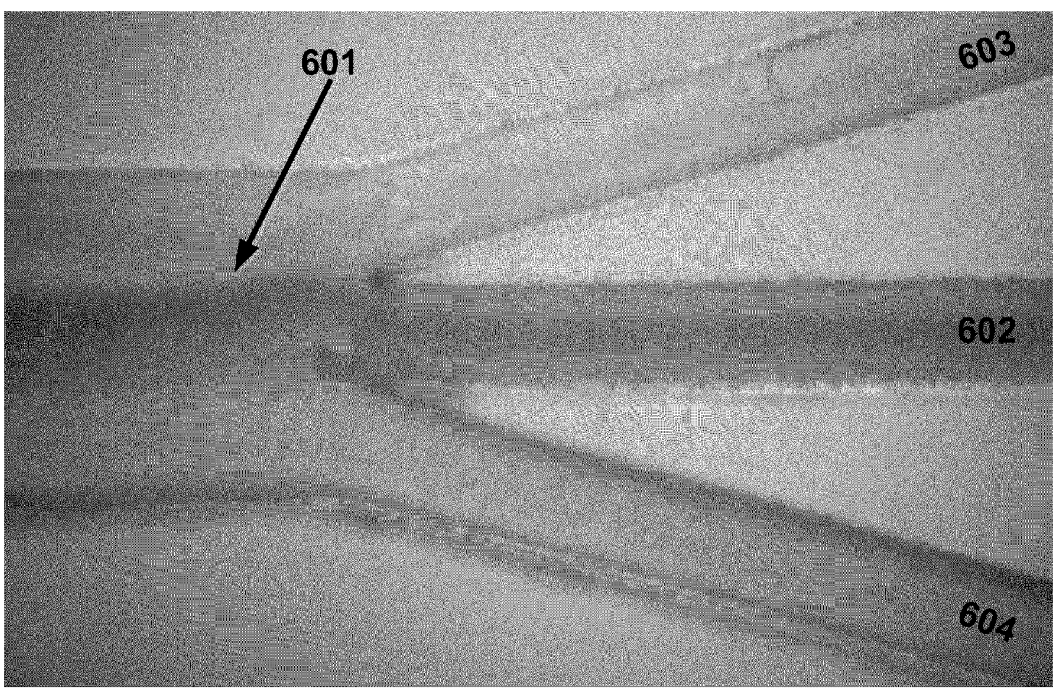

FIG. 6A is a top view of a separation channel 600, as depicted in FIG. 2, in which fluid is flown through the separation channel 600 without the application of the standing acoustic wave. The separation channel 600 includes three outlets 602, 603 and 604. As with FIG. 5A, particles suspended in the fluid are homogeneously distributed throughout the fluid, and thus are not readily discernible in the image. The particles flow substantially evenly out of all three outlets 602, 603 and 604.

In contrast, FIG. 6B is a top view of the separation channel 600, as depicted in FIG. 2, after the application of a standing acoustic wave, according to one illustrative embodiment.

In FIG. 6B, as a result of the standing acoustic wave, the particles 601 suspended in the fluid are aligned with the middle of the separation channel 600. Once aligned with the middle of the separation channel 600, the particles 601 exit the separation channel 600 through the middle outlet 602. The remaining fluid, substantially devoid of particles, exits the separation channel through the side outlets 603 and 604.

Figure 7:
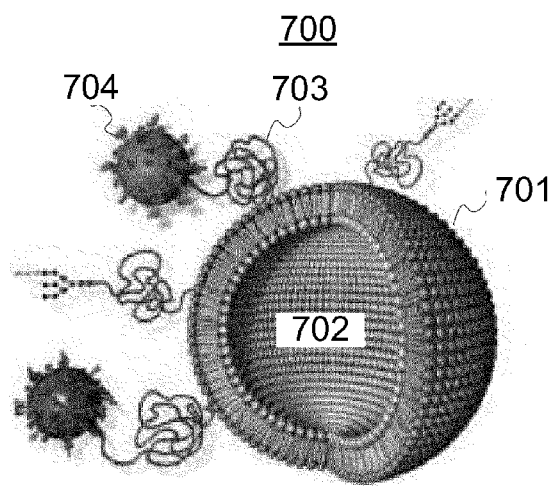
FIG. 7 is a cut away of a lipid-based capture particle, according to one illustrative embodiment.

FIG. 7 is an illustrative example of a lipid bilayer capture particle 700. The capture particle 700 includes a lipid bilayer 701 encapsulating a fluid 702. Anchored in the lipid bilayer are affinity particles 703. The affinity particles bind and capture undesirable particles 704.

More specifically, the lipid bilayer 701 forms a liposomal capture particle. In some implementations, the lipids may be, but are not limited to dilauroyl-glycero-phosphoglycerol and dilauroyl-glycero-phosphocholine. The capture particle is tuned for acoustically induced mobility. Entities that differ in size, density, and/or compressibility have the greatest differential mobility in acoustic fields and thus are the most readily separable. Therefore, in some implementations, the size, density, and/or compressibility of the capture particles is modified to distinguish the capture particle from the formed elements of blood. The acoustic mobility of a particle is proportional to its volume. For example, in some implementations, the capture particles are about 1 µm in diameter. In other implementations they are between about 2 and about 5 µm in diameter. In implementations that adjust the compressibility of the capture particle, the rigidity of the capture particle can be adjusted by controlling the lipid components in the bilayer. The length and saturation of the lipid hydrocarbon tail, cross-linking of the hydrophobic domains, and/or the inclusion of cholesterol can all affect the fluidity and compressibility of a liposome. In other implementations, the density of the liposome is engineered by encapsulating an acoustically active fluid 702. In these implementations the acoustical active molecule can be a FDA-approved contrast agent, glycerine, castor oil, coconut oil, paraffin, air, and/or silicone oil. In other implementations, all the above described characteristics are manipulated to create a capture particle with the greatest possible difference in contrast factor compared to a formed element.

As described above, the acoustically induced mobility of a particle is based on the contrast factor of the particle. For a liposomal based capture particle, the contrast factor is dominated by the properties of the encapsulated fluid. The contrast factor is based on the bulk modulus (K) and density ($\rho$) of the encapsulated fluid. When suspended in blood, the contrast factor ($\phi$) for a capture particle, encapsulating a specific fluid, is calculated with the below equation:

$$\varphi = \frac{5\rho - 2 \cdot 1.02}{2\rho + 1.02} + \frac{2.2}{K}$$

Table 1 provides the $\rho$, K, and then calculated $\phi$-factor based on the above equation.

TABLE 1

| Calculated Contrast Factors | | | | |
|---|---|---|---|---|
| | Materials | $\rho$ (g/ml) | K(Gpa) | $\phi$ |
| Encapsulated Fluids | glycerine | 1.25 | 4.7 | +0.73 |
| | castor oil | 1.03 | 2.06 | −0.06 |
| | coconut oil | 0.92 | 1.75 | −0.36 |
| | paraffin | 0.80 | 1.66 | −0.58 |

TABLE 1-continued

Calculated Contrast Factors

| | Materials | ρ (g/ml) | K(Gpa) | φ |
|---|---|---|---|---|
| | silicone oil | 1.04 | 1.09 | −1.00 |
| | air | 0.002 | 1.4 | −3.55 |
| Formed | white blood cell | 1.02 | 2.5 | +0.12 |
| Elements | red blood cell | 1.10 | 3.0 | +0.34 |

In some implementations, such as the implementation of FIG. 3, the capture particles have a contrast factor that is lower in magnitude, but still of the same sign as the formed elements. In these implementations, the low contrast factor of the capture particles can be achieved by making the capture particles sufficiently small to reduce their contrast factor to below that of the formed elements.

As illustrated in FIG. 7, affinity molecules 703 are embedded in the lipid bilayer 701. In some implementations, these affinity molecules are glycoconjugates. The glycoconjugates enable the capture and retention of all major classes of pathogens, including bacteria and viruses. In some implementations, the affinity molecules 703 also bind to toxins and pro-inflammatory cytokines In some implementations, affinity molecules 703 are designed to universally capture gram-negative and gram-positive bacteria, virus, toxins, by exploiting that: 1) pathogens express unusual surface N- and O-linked glycan structures that can be targeted by glycan-binding proteins or lectins and 2) many pathogens and toxins bind to charged polysaccharides, especially those of the heparan sulfate family, that are present on the cell surface of mammalian cells. Some implementations employ glycoconjugate capture agents that have two components: a modified, non-anticoagulant heparin fragment that nevertheless maintains high affinity, multivalent binding properties, and a glycan-binding protein that binds to surface N- and O-linked glycans present on the surface of pathogens. In other implementations, the glycan structure is a lectin. For example the lectin can be, but is not limited to: type 2 membrane receptors such as DC-SIGN, DC-SIGNR, and Langerine; collectins such as pulmonary surfactant proteins (SP-D, SP-Al), mannose binding lectin, and collectin-Kl; and macrophage mannose receptors. In other implementations, the affinity molecule is an antibody.

The affinity particles are anchored to the liposomal surface so their concentration, valency, and distribution can be controlled. This is particularly relevant since pathogen-receptor interactions are often multivalent and the receptor configuration impacts overall avidity. In some implementations, the affinity molecule is attached to an anchor that is incorporated into the lipid bilayer, so the embedded functional groups remain in close proximity but are free to rotate and rearrange. Lipid anchors are favored because the molar ratio of derivatized lipids incorporated can be controlled. Lectins are incorporated by solublizing a surfactant with pre-formed liposome suspensions, through direct addition of fatty acids to lysine residues, or by modification with hydrophobic anchor lipids such as Nglutaryl-phosphotidy-lethanolamine (NGPE).

Figure 8:
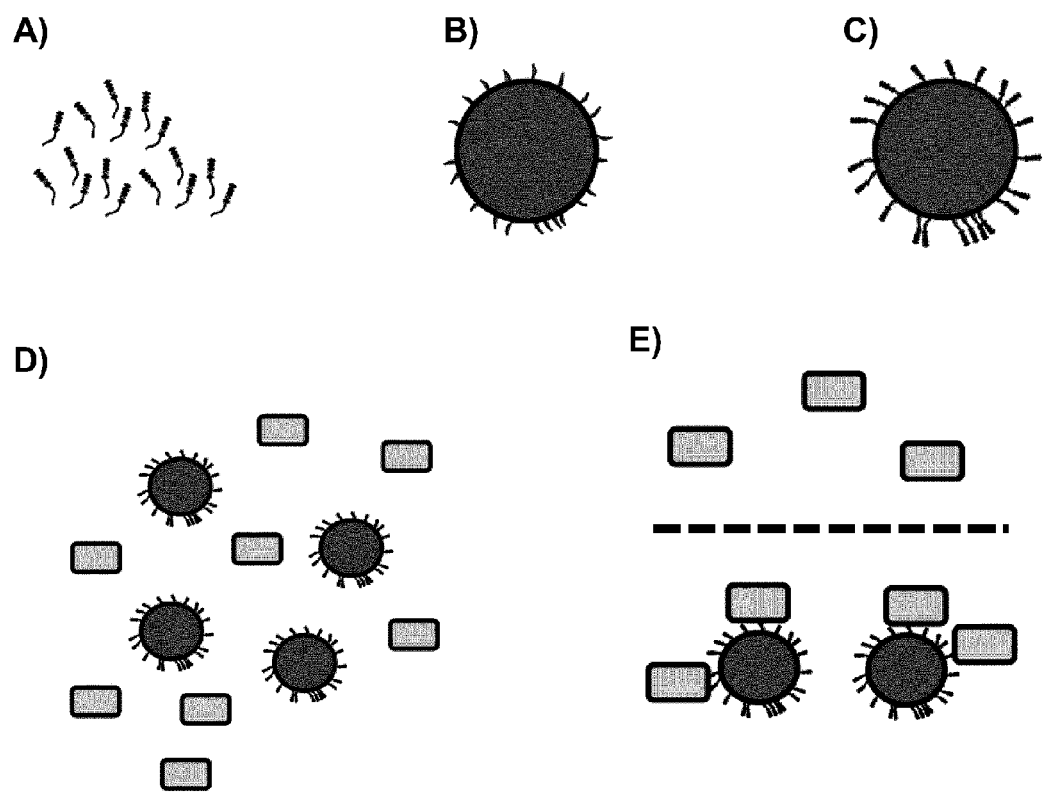
FIGS. 8A-E are illustrations of the components and use for a capture particle, as depicted in FIG. 7, according to one illustrative embodiment.

FIG. 8 illustrates an overview of the process of making and using a capture particle. The affinity molecules of FIG. 8A are embedded in the liposome of FIG. 8B to produce a affinity coated liposome as illustrated in FIG. 8C. Next, the capture particle are combined with a blood or other fluid containing undesirable particles. The undesirable particles then bind to the capture particles. FIG. 8E illustrates, bound undesirable particles can then be removed from the fluid by acoustically moving the capture particles whereas unbound undesirable particle are not removed from the fluid.

Figure 9:
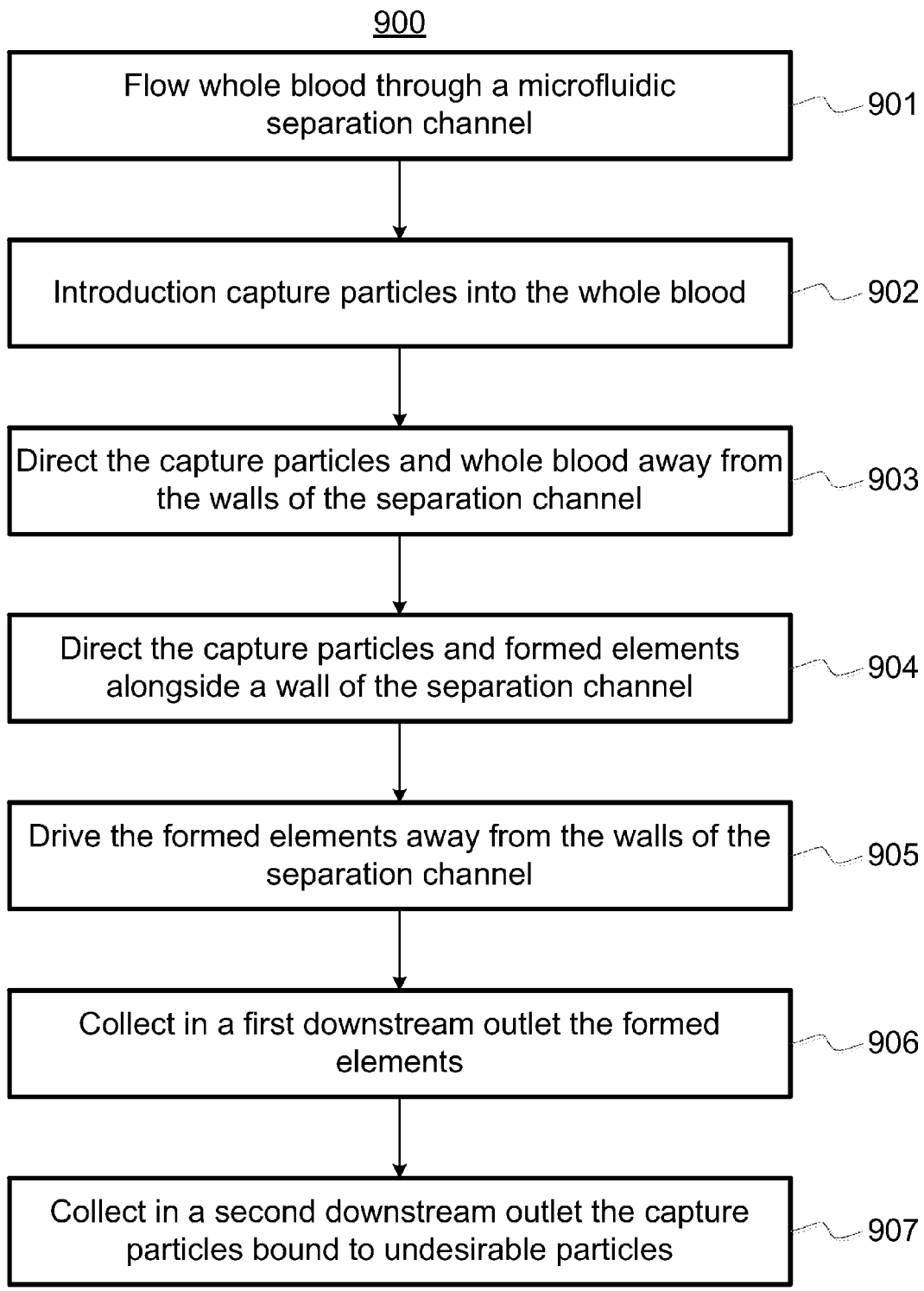
FIG. 9 is a flow chart of a method for cleansing blood with a two-stage separation channel, as depicted in FIG. 3, according to one illustrative embodiment.

FIG. 9 is a flow chart of a method 900 to cleanse blood from undesirable particles in a blood cleaning separation channel similar to the two-stage device described in FIG. 3. First whole blood is flowed trough a microfluidic separation channel (step 901). Capture particles are introduced into the whole blood (step 902). Then, formed elements of the blood and the capture particles are directed away from the walls of the separation channel (step 903). Next, the capture particles and formed elements are directed alongside a wall of the separation channel (step 904). Then, formed elements are driven away from the walls of the separation channel (step 905). Finally, the formed elements are collected in a first downstream outlet and the capture particles are collected in a second downstream outlet (steps 906 and 907, respectively).

Referring to FIGS. 3 and 9, the method of cleansing blood includes flowing whole blood through a microfluidic separation channel (step 901). The whole blood contains plasma; a plurality of formed elements such as red blood cells, white blood cells, and platelets; and undesirable particles. In some implementations, the whole blood is flowed through a plurality of microfluidic separation channels, such as the network of channels 300, connected to one another by a manifold system, while in other implementations a single separation channel is used. In some implementations, the whole blood is extracted from a patient. In other implementations the whole blood is collected from a patient or donor and stored prior to cleansing.

Capture particles are introduced into the whole blood (step 902). In some implementations, the capture particles are introduced into the whole blood at the first inlet 301 of the separation channel depicted in FIG. 3. In other implementations, the capture particles are introduced into the device's manifold system or in a mixing chamber upstream from the manifold. After introduction into the whole blood, the capture particles begin to bind to the undesirable particles in the whole blood. For example, a capture particle configured to remove a specific bacteria from the whole blood will selectively bind to the bacteria.

Next, the method 900 continues with the capture particles and the formed elements of the whole blood, which are, originally, substantially-evenly dispersed throughout the whole blood, being directed away from the walls of the separation channel (step 903) and aggregated into alignment at about the center of the separation channel. In some implementations, such as the implementation in the network 300 as described above, this is done with a first bulk transducer 302 imparting a standing acoustic wave across the channel transverse to the direction of flow within the channel in an upstream portion 308, resulting in a pressure node at about the center of the separation channel. In such implementations the contrast factor of the capture particles has the same sign as that of the formed elements, thus the formed elements and capture particles move in tandem towards the pressure node. This initial aggregation of particles along a common axis enables later separation of the capture particles from the formed elements of blood due based on their differential acoustophoretic mobilities.

As discussed above in reference to network 300, after an initial aggregation (step 903), the method 900 continues with the capture particles and formed elements of blood being directed alongside a downstream wall of the separation channel (step 904). In some implementations, such as that of network 300, this is accomplished by a shift in the separation channel such that the downstream portion of the separation channel is significantly aligned with the middle of the upstream portion of the separation channel.

As depicted in FIG. 3 above, in the downstream portion 309, the method 900 continues with the formed elements being driven way from the walls of the separation channel (step 905). As mentioned above, in some implementations, the contrast factor of the formed elements and the capture particles have the same sign but are of different magnitudes. Thus, the formed elements will migrate away from the wall at a faster rate than the capture particles and undesirable particles. In other implementations, the capture particles are designed to have a contrast factor magnitude larger than the formed elements of blood, thus the capture particles move away from the wall at a faster rate than the formed elements.

The method 900 concludes when the formed elements are collected in a first downstream outlet (step 906) and the capture particles being collected in a second downstream outlet (step 907). As described above in relation to network 300, the second downstream outlet 306 is configured to collect fluid containing capture particles substantially devoid of formed elements. In some implementations, this is achieved by configuring the width of the second downstream outlet 306 to be slightly less than d, x), the distance the formed elements travel in response to the standing acoustic wave given a flow rate off and a distance x from the point of application of the standing acoustic wave. Thus the formed elements, having been driven d(f, x) away from the of the separating channel will be collected in the first downstream outlet 307.

Figure 10:
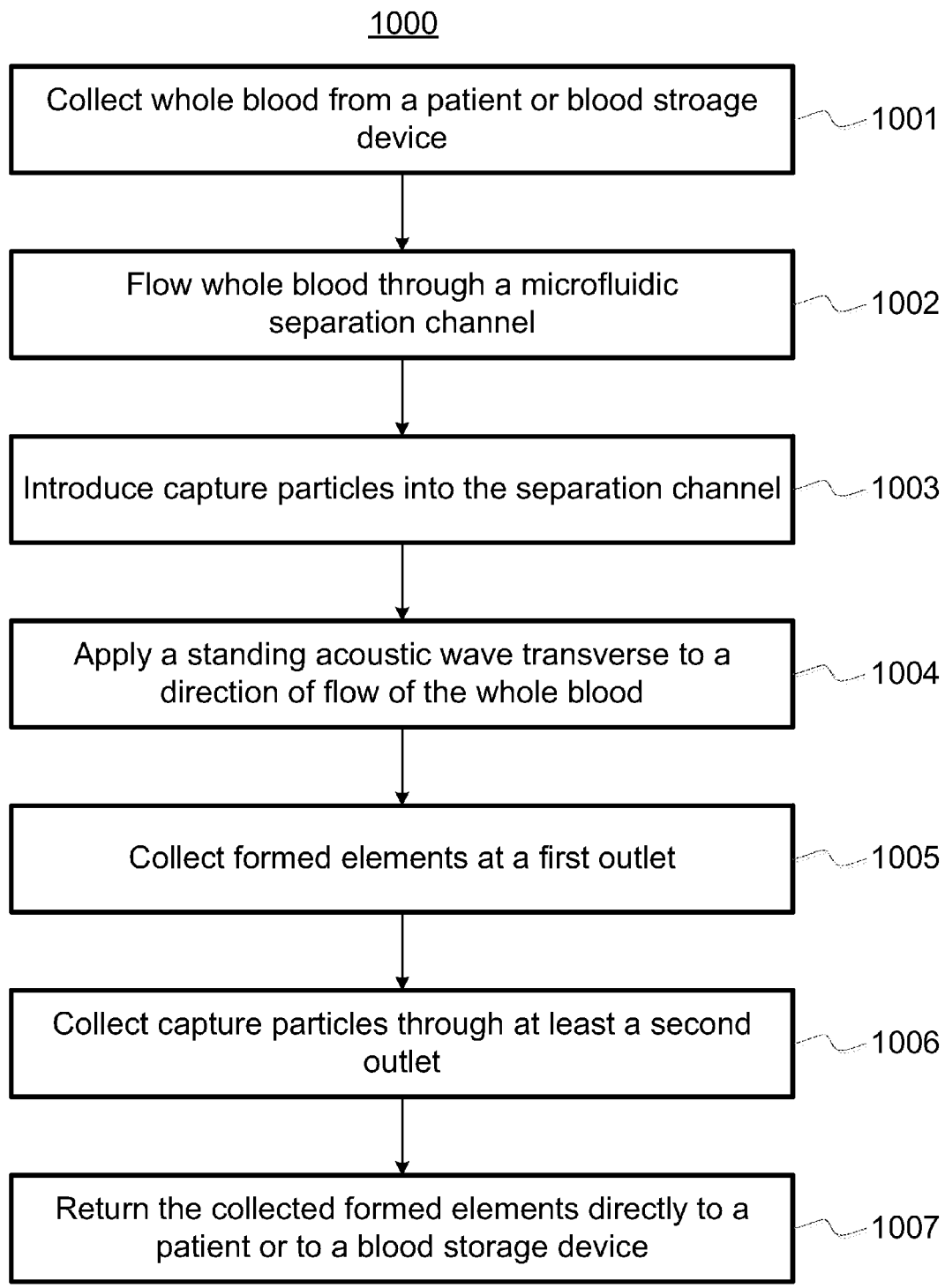
FIG. 10 is a flow chart of a method for cleansing blood with a single-stage separation channel, as depicted in FIG. 2, according to one illustrative embodiment.

FIG. 10 is a flow chart of a method for cleansing blood with a single-stage microfluidic separation channel (1000). First, whole blood is collected (step 1001). Then whole blood is flowed into an inlet of a single-stage microfluidic separation channel, as depicted in FIG. 2 (step 1002). Next, a plurality of capture particles are introduced into the whole blood (step 1003). Then a standing acoustic wave is applied to the separation channel (step 1004). The formed elements are then collected in a first outlet (step 1005). Next, the capture particles are collected in a second outlet (step 1006). Finally, the cleansed blood is returned to a storage container or returned directly to the patient (step 1007).

Referring to FIGS. 1, 2 and 10, the method 1000 of cleansing blood with a single-stage microfluidic separation channel 200 begins by collecting whole blood. In some implementations, the whole blood is collected from a patient 101, and then directly introduced into the blood cleansing system 100. In other implementations, the whole blood is collected from a patient 101 and then stored for later cleansing.

Next, the method 1000 of cleansing blood with a single-stage microfluidic separation channel 200 continues by flowing whole blood into the inlet of a microfluidic separation channel (step 1002). The whole blood contains a plurality of formed elements, plasma, and a plurality of undesirable particles. In some implementations, the undesirable particles can be toxins, bacteria, and/or viruses. In some implementations, a single microfluidic separation channel is used, while in others a plurality of single-stage separation channels are used in conjunction to accommodate greater blood flow throughput.

The method 1000 continues with the introduction of a plurality of capture particles into the whole blood (step 1003). In some implementations, the constituent components of capture particles are injected into a separation channel with a micronozzle and spontaneously form capture particles as injected into the separation channel. In other implementations, the capture particles are prefabricated and then introduced into the whole blood. In some implementations, the capture particles are introduced into the whole blood after the whole blood enters the separation channel through the first inlet 202. In yet other implementations, the capture particles are introduced into the whole blood before the blood enters through the first inlet 202 of the separation channel 200. In some implementations, the capture particles are microbeads and/or lipid based liposomes.

Next, the method 1000 continues with the applying of a standing acoustic wave to the separation channel (step 1004). The standing acoustic wave is applied transverse to a direction of flow of the whole blood through the separation channel 200. In some implementations, the formed elements and capture particles have contrast factors with different signs. Thus, the application of the standing acoustic wave causes the formed elements to aggregate about the central axis of the separation channel and the capture particles to aggregate along at least one wall of the separation channel, as depicted in FIG. 2. In other implementations the standing acoustic wave causes the formed elements to aggregate along at least one wall of the separation channel and the capture particles to aggregate about the central axis of the separation channel.

Then, the method 1000 continues with the collecting of the formed elements of the whole blood in a first outlet (step 1005). In some implementations, as depicted in FIG. 2, a first outlet 204 is aligned with the central axis of the separation channel allowing the outlet to collect the formed elements as they aggregate and flow down the central axis of the separation channel. Similarly, the method continues with the collecting of the capture particles in a second outlet (step 1006). In some implementations, the end of the separation channel has at least a second outlet channel 206 and 207 aligned with at least one wall of the separation channel. As the capture particles are driven towards the antipressure notes along the walls of the separation channel, they are collected by the outlets channels 206 and 207 aligned with the walls of the separation channels. In some implementations, the standing acoustic wave is adjusted such that the formed particle align along the walls of the separation channel and the capture particles align with the central axis of the separation channel. In such an implementation, the formed elements are funneled into outlets along the wall of the separation channel and the capture particles are funneled into an outlet aligned with the central axis of the separation channel. In some implementations, the outlet channels 206 and 207 terminate in individual outlets or merge to terminate into a single outlet 205.

The method 1000 concludes with the reintroduction of the cleansed blood into a patient 101 or storage (step 1007). In some implementations, such as system 100, the whole blood is collected directly from a patient and then reintroduced to the patient 101. In some implementations, the cleansed blood is reheated to body temperature before being reintroduced into the patient 101. In other implementations, the cleansed blood is collected in a storage container for later reintroduction into a patient 101.

What is claimed is:

1. A blood cleansing device configured for microfluidic separation of undesirable particles from formed elements of whole blood, the blood cleansing device comprising:
   at least one separation channel configured to provide (a) a first portion where a first standing acoustic wave drives the formed elements of the whole blood and the captures particles along a first longitudinal axis parallel and against to a wall of the at least one separation channel and (b) a second portion where a second standing acoustic wave drives the formed elements of the whole blood toward a second longitudinal axis in an interior region of the second portion and parallel to the wall of the at least one separation channel, the at least one separation channel further comprising:
- a first inlet configured to introduce the whole blood and the plurality of capture particles into the first portion of the at least one separation channel, the whole blood including plasma, the plurality of formed elements having a first positive contrast factor and the plurality of undesirable particles having a second positive contrast factor less than the first positive contrast factor;
- a first outlet positioned within the separation channel downstream from the first inlet;
- a second outlet for the removal of the plurality of capture particles bound to at least a portion of the plurality of undesirable particles, the second outlet positioned against the wall of the at least one separation channel and downstream of the first inlet;
- a second inlet positioned within the separation channel downstream of the first outlet and upstream of the second outlet; and
- a third outlet for the removal of the plurality of formed elements, the third outlet positioned parallel with the second longitudinal axis in the interior region of the second portion and parallel to the wall of the at least one separation channel in the second portion of the at least one separation channel and positioned away from the wall of the at least one separation channel a first distance proportional to a distance from the second standing acoustic wave, a flow rate of the whole blood, and the first negative contrast factor, wherein the at least one separation channel is configured to separate the plurality of undesirable particles from the formed elements by:
  (i) aggregating the plurality of undesirable particles bound to the plurality of capture particles at a first pressure node in the first portion of the at least one separation channel and aligned with the first longitudinal axis parallel and against to a wall of the at least one separation channel;
  (ii) driving the formed elements of the whole blood toward a second pressure node in the second portion of the at least one separation channel and aligned with the second longitudinal axis in the interior region of the second portion and parallel to the wall of the at least one separation channel, wherein the formed elements are driven at least the first distance away from the wall and into the third outlet; and
  (iii) driving the plurality of capture particles bound to the plurality of undesirable particles toward the second pressure node in the second portion of the at least one separation channel aligned with the second longitudinal axis a second distance less than the first distance.

2. The blood cleansing device of claim 1, comprising at least a second separation channel and a third separation channel, wherein:
- a first outlet of the second separation channel is configured to carry fluid from the second separation channel to the second inlet of the separation channel, and
- a second inlet of the third separation channel is configured to receive fluid from the first outlet of the separation channel.

3. The blood cleansing device of claim 1, comprising a microfluidic injector for introducing, into the separation channel, the plurality capture particles configured to bind to the undesirable particles.

4. The blood cleansing device of claim 3, wherein the plurality of capture particles are lipid-based and the microfluidic injector comprises one of a microfluidic nozzle and a porous membrane coupled to a lipid reservoir.

5. The device of claim 1, wherein the separation channel is formed in a substrate comprising one of polystyrene, glass, polyimide, acrylic, polysulfone, and silicon.

6. The blood cleansing device of claim 1, comprising an acoustic transducer positioned adjacent to the separation channel and configured to impose the first standing wave transverse to the length of the first portion of the at least one separation channel, wherein the first standing wave is configured to focus the formed elements and the plurality of the undesirable particles bound to the plurality of capture particles towards an interior region of the first portion of the at least one separation channel.

7. The blood cleansing device of claim 6, comprising a second acoustic transducer positioned adjacent to the second portion of the at least one separation channel and configured to impose the second standing wave transverse to the length of the second portion of the at least one separation channel, wherein the second standing wave is selected such that the formed elements are be driven toward the second pressure node at a rate that is faster than a rate at which the second standing wave drives the undesirable particles bound to the capture agents toward the second pressure node.

8. The blood cleansing device of claim 6, wherein the second outlet is positioned sufficiently downstream within the second portion of the at least one separation channel that in operation, a greater percentage of the undesirable particles that are bound to the plurality of capture particles flows out of the second outlet than out of the third outlet and a greater percentage of the formed elements flows out of the third outlet than out of the second outlet.

9. The device of claim 1, wherein the first portion of the separation channel comprises an aggregation point, and the first portion of the at least one separation channel is configured such that a width of the first portion of the at least one separation channel at the aggregation point is half the wavelength of an acoustic wave acting on the whole blood.

10. The device of claim 1, wherein the at least one separation channel comprises walls having a thickness at a particle aggregation point that is a multiple of one quarter of the wavelength of an acoustic wave acting on the walls of the at least one separation channel.

11. The device of claim 1, wherein the height of the at least one separation channel at a particle aggregation point is less than one quarter of the wavelength of an acoustic wave acting on the particle aggregation point.

12. A method of cleansing blood comprising
- flowing whole blood, containing a plurality of undesirable particles, formed elements having a second contrast factor, and plasma, through a microfluidic separation channel;
- introducing capture particles having a first contrast factor less than the second contrast factor, from a reservoir, into whole blood such that the capture particles can bind to at least a plurality of the undesirable particles;
- aggregating, in a first portion of the separation channel, with a first standing acoustic wave, the formed elements of the whole blood and the captures particles to a first aggregation axis a first distance from a first wall of the separation channel in a second portion of the separation channel;
- directing, downstream of the first portion of the separation channel, the captures particles and the formed elements alongside the first wall of the separation channel that is aligned with the first aggregation axis of the separation channel;
driving, in the second portion of the separation channel prior to a second outlet, with a second standing acoustic wave, the formed elements of the flowing whole blood at a first rate away from the wall of the separation channel that is aligned with the first aggregation axis of the separation channel, the formed elements driven from the wall of the separation channel a first distance greater than a width of the second outlet and into a third outlet; and
driving, in the second portion of the separation channel and prior to the second outlet, with the second acoustic wave, the capture particles at a second rate, different than the first rate, a second distance less than the first distance such that the capture particles flow out of the second outlet as the formed elements flow out of third outlet of the separation channel.

13. The method of claim 12, wherein the capture particles comprise an affinity molecule anchored to a lipid layer encapsulating a fluid.

14. The method of claim 13, wherein the fluid has a density less than about 1 g/cm$^3$.

15. The method of claim 13, wherein affinity molecule, lipid, and fluid are mixed in the reservoir prior to their injection into the separation channel.

16. The method of claim 15, wherein injecting the capture particles comprises injecting the mixture of the affinity molecule, lipid, and fluid through a nozzle such that the lipid forms a lipid layer surrounding the fluid.

17. The method of claim 12, wherein the capture particle comprises a polystyrene bead.

18. The method of claim 12, wherein the capture particles have significantly different acoustophoretic mobility than that of formed elements of blood.

19. The method of claim 12, wherein the capture particles are less than 10 μm and greater than 2 μm in diameter.

20. The method of claim 12, wherein the formed elements of blood comprises at least one of red blood cells, white blood cells, and platelets.

21. The method of claim 12, further comprising unbinding the capture particles from the undesirable particles after flowing through the third outlet and reinjecting the unbound capture particles into the separation channel.

22. The method of claim 12, further comprising:
extracting whole blood from a patient prior to flowing the whole blood through the separation channel, the extracted whole blood having a first concentration of undesirable particles; and
reintroducing whole blood with fewer undesirable particles back into the patient after flowing whole blood through the plurality of microchannels.

23. A blood cleansing device comprising:
a separation channel having a first portion and a second portion downstream of the first portion, the separation channel comprising:
a first inlet configured to introduce flowing whole blood into the first portion of the separation channel, the whole blood including plasma, a plurality of formed elements each having a first positive contrast factor and a plurality of undesirable particles;
a first outlet at the downstream of the first inlet and positioned substantially along the longitudinal axis of the separation channel;
a second outlet in the second portion of the separation channel and positioned adjacent a first wall of the separation channel, the second outlet positioned for the removal of the plurality of undesirable particles bound to a plurality of capture particles; and
a first acoustic transducer positioned adjacent to the separation channel for imposing a first standing acoustic wave transverse to the flow of blood through a particle migration region of the separation channel in the first portion of the separation channel;
a second acoustic transducer positioned adjacent to the separation channel for imposing a second standing acoustic wave transverse to the flow of blood through a second particle migration region of the separation channel in the second portion of the separation channel, the second standing acoustic wave configured to drive the formed elements a first distance away from the first wall of the separation channel at a first rate and into a third outlet and the capture particles bound to the undesirable particles a second distance that is less than the first distance away from the first wall of the separation channel at a second rate and into the second outlet; and
a capture particle injector configured to introduce a plurality of lipid-based capture particles into the whole blood before the blood reaches the particle migration region of the separation channel, wherein the lipid-based capture particles each have a second contrast factor and encapsulate a fluid that is acoustically active with respect to the whole blood such that the plurality of formed elements are driven at a first rate responsive to the first contrast factor and the plurality of lipid-based capture particles are driven toward an aggregation axis of the separation channel at a second rate responsive to the second contrast factor when the standing acoustic wave is imposed.

24. The blood cleansing device of claim 23, comprising a reservoir in fluidic communication with the capture particle injector.

25. The blood cleansing device of claim 23, wherein the plurality of captures particles are lipid-based capture particles.

26. The blood cleansing device of claim 23, wherein the reservoir contains a mixture of materials, which when directed by the capture particle injector into the whole blood, form lipid-based capture particles.

27. The blood cleansing device of claim 26, wherein the materials in the mixture comprise a affinity molecule, a lipid, and a fluid with a density less than about 1 g/cm$^3$.

28. The blood cleansing device of claim 23, wherein the lipid-based capture particles have significantly different acoustophoretic mobility than that of formed elements of blood.

29. The blood cleansing device of claim 23, wherein the capture particle injector comprises a microfluidic nozzle.

30. The blood cleansing device of claim 23, wherein the capture particle injector comprises a porous membrane.

31. The blood cleansing device of claim 23, wherein the second and third outlets merge at a fourth outlet.

32. A method of cleansing blood comprising:
flowing whole blood, including plasma, a plurality of formed elements having a first positive contrast factor, and a plurality of undesirable particles, into an inlet of a microfluidic separation channel;
introducing a plurality of lipid-based capture particles, each of the plurality of lipid-based capture particles encapsulating a fluid that is acoustically active with respect to the whole blood and having a second positive contrast factor less than the first positive contrast factor, into the whole blood such that the lipid-based capture particles bind to a plurality of the undesirable particles;

aggregating, with a first standing acoustic wave, the plurality of lipid-based capture particles and the formed elements at a first pressure node in a first portion of the separation channel; and driving, with a second standing acoustic wave transverse to a direction of flow of the whole blood through the separation channel, the formed elements toward an axial center of the separation channel a first distance from at least one wall of the separation channel, at a first rate, and into an outlet of the separation channel and the plurality of lipid-based capture particles bound to the plurality of undesirable particles a second distance less than the first distance, at a second rate, and into a different outlet of the separation channel.

33. The method of claim 32, further comprising collecting formed elements of the whole blood at a first outlet positioned at a downstream end of the separation channel at about the axial center of the separation channel.

34. The method of claim 32, further comprising collecting capture particles through at least a second outlet positioned at a downstream end of the separation channel adjacent to the at least one wall along which the capture particles are aggregated.

35. The method of claim 32, wherein the at least one wall comprise at least one side wall of the separation channel.

36. The method of claim 32, wherein the at least one wall comprises at least one of the top and bottom walls of the separation channel.

37. The method of claim 32, wherein the capture particles comprise an affinity molecule anchored to a lipid layer encapsulating the acoustically active fluid.

38. The method of claim 37, wherein the fluid has a density less than about 1 g/cm$^3$.

39. The method of claim 37, wherein affinity molecule, lipid, and fluid are mixed in the reservoir prior to their injection into the separation channel.

40. The method of claim 37, wherein injecting the capture particles comprises injecting the mixture of the affinity molecule, lipid, and fluid through a nozzle such that the lipid forms a lipid layer surrounding the acoustically active fluid.

41. The method of claim 32, wherein the capture particles are less than 5 μm in diameter.

42. The method of claim 32, wherein the capture particles are less than 2 μm in diameter.

43. The method of claim 32, wherein the formed elements of blood comprises at least one of red blood cells, white blood cells, and platelets.

44. The method of claim 32, further comprising:

extracting whole blood from a patient prior to flowing the whole blood through the separation channel, the extracted whole blood having a first concentration of undesirable particles; and reintroducing whole blood with fewer undesirable particles back into the patient after flowing whole blood through the plurality of microchannels.

45. A method of cleansing blood comprising:

flowing a suspension, including a plurality of target particles having a first positive contrast factor and a plurality of undesirable particles suspended in a fluid into an inlet of a microfluidic separation channel;

introducing into the suspension a plurality of lipid-based capture particles, each of the plurality of lipid-based capture particles encapsulating a fluid that is acoustically active with respect to the suspension and having a second positive contrast factor less than the first positive contrast factor, such that the lipid-based capture particles bind to a plurality of the undesirable particles;

aggregating, with a first standing acoustic wave, the plurality of lipid-based capture particles and the plurality of target particles at a first pressure node in a first portion of the separation channel; and driving, with a second standing acoustic wave transverse to a direction of flow of the suspension through the separation channel, the target particles toward an axial center of the separation channel a first distance from at least one wall of the separation channel, at a first rate, and into an outlet of the separation channel and driving the plurality of lipid-based capture particles bound to the plurality of undesirable particles a second distance that is less than the first distance from the at least one wall of the separation channel, at a second rate, and into a different outlet of the separation channel.

46. The method of claim 13, wherein the lipid layer is a lipid bilayer.

47. The method of claim 16, wherein the lipid layer forms a liposome.

48. The method of claim 37, wherein the lipid layer is a lipid bilayer.

49. The method of claim 40, wherein the lipid layer forms a liposome.

* * * * *